(12) United States Patent
Truett

(10) Patent No.: US 6,437,119 B1
(45) Date of Patent: Aug. 20, 2002

(54) COMPOUNDS FORMED FROM TWO OR THREE ANTIBIOTICS AND THEIR PROCESSES OF PREPARATION

(76) Inventor: William Lawrence Truett, P.O. Box 2067, Lebanon, NH (US) 03766

( * ) Notice: Subject to any disclaimer, the term of this patent is extended or adjusted under 35 U.S.C. 154(b) by 7 days.

(21) Appl. No.: 09/618,106

(22) Filed: Jul. 17, 2000

Related U.S. Application Data

(63) Continuation-in-part of application No. 09/304,715, filed on May 4, 1999, now abandoned.
(60) Provisional application No. 60/084,586, filed on May 7, 1998.

(51) Int. Cl.$^7$ .................. C07D 519/06; A61P 31/04; A61K 31/546; A61K 31/431
(52) U.S. Cl. .................. 540/215; 540/223; 540/226; 540/227; 540/230; 540/310; 540/316; 540/318; 540/355

(58) Field of Search .................. 540/316, 318, 540/310, 223, 226, 227, 230, 215, 355

(56) References Cited

U.S. PATENT DOCUMENTS

| | | | |
|---|---|---|---|
| 4,404,201 A | 9/1983 | Haskell | 424/246 |
| 4,546,716 A | 10/1985 | Machida | 544/21 |
| 5,180,719 A | 1/1993 | White | 540/314 |
| 5,232,918 A | 8/1993 | Arnould | 514/202 |
| 5,281,703 A | 1/1994 | White | 520/302 |
| 5,336,768 A | 8/1994 | Albrecht | 540/222 |
| 5,693,791 A | 12/1997 | Truett | 540/222 |

*Primary Examiner*—Mark L. Berch
(74) *Attorney, Agent, or Firm*—Herbert M. Wolfson

(57) ABSTRACT

Processes for preparing compounds having two or three antibiotic functionalities using quinolone derivatives, β-lactams and vancomycin and the like as the starting materials and chloride linking agents; and the novel compounds prepared by these processes, are disclosed.

2 Claims, No Drawings

COMPOUNDS FORMED FROM TWO OR THREE ANTIBIOTICS AND THEIR PROCESSES OF PREPARATION

CROSS-REFERENCE TO PRIOR APPLICATIONS

This application is a continuation-in-part of U.S. application Ser. No. 09/304,715 filed May 4, 1999 ABN which claimed the benefit of U.S. Provisional Application No. 60/084,586 filed May 7, 1998.

BACKGROUND OF THE INVENTION

The present invention is concerned with an improved process for forming a single composition from two antibiotics, e.g., from Quinolone antibiotics and Beta-lactam antibiotics, as Penicillin and Cephalosporin types, and also with the addition of steps to add a third antibiotic component to the bi-component composition, the third ($3^{rd}$) antibiotic drawn from the group Vancomycin, Erythromycin, Azithromycin, an Aminoglycoside as Gentamycin, A Tetracycline, Clindamycin, and Chloramphenicol.

The value of a composition wherein a trio of individual antibiotics are joined is that the bacterial infective agent will simultaneously be attacked by agents which are known to attack the cell-wall producing enzyme of the bacteria, and inhibit the DNA gyrase enzyme, and inhibit the enzyme that controls bacterial protein synthesis.

The value of this composition of three antibiotic functional types is that it will further be seen that resistant strains will be very unlikely to develop due to the necessity of simultaneously overcoming three attacking agents.

There is evidence for this statement in the present day success of several cocktails—combinations—of drugs which are being utilized to treat AIDS patients, TB patients and other similar examples. In the case of the AIDS virus, a combination of two retroviral inhibitors, as AZT and DDI are being employed plus one of several viral protease inhibitors as invirase. In the case of TB patients a cocktail of four drugs is being utilized successfully to overcome resistant TB strains. Further, White, U.S. Pat. No. 5,281,703, has shown that a composition containing a Cephalosporin and a Quinolone antibiotic is very effective in treating certain pneumonias. Pirie, U.S. Pat. No. 4,351,840, has also shown that the composition of a Penicillin with a Beta-lactam protective inhibitor enhances the value of Penicillin.

In U.S. Pat. No. 5,693,791, whose disclosure is incorporated by reference herein, I have disclosed the process of linking a wide variety of antibiotic moieties, two at a time, using diisocyanates, dianhydrides, diacid chlorides, diepoxides, carbodiiamides and the like as the linking reagents.

There are prior for linking two antibiotics into a single composition, e.g., quinolone antibiotics with the beta-lactam, cephalosporin. However, the processes are complex: the reagents are dangerous; and they are all expensive. They are compared in the following table:

1. White, Norwich Eaton Pharmaceutical, U.S. Pat. No. 5,180,719
   A. Links quiniolines and cephalosporins
   B. Linking agent-phosgene
   C. Synthesis steps—multiple
   D. Activity—good, human tests
   E. Cost—high
2. Albrecht, Hoffman-LaRoche, U.S. Pat. No. 5,336,768
   A. Links quinolones and cephalosporins
   B. Linking agent—phosgene
   C. Synthesis steps—multiple
   D. Activity—good, human tests
   E. Cost—high
3. Machida, Eisai (Japan), U.S. Pat. No. 4,546,176
   A. Links cephalosporin with substituted quinolone nucleus (not quinolone antibiotic)
   B. Linking agent—acid chloride of quinolone
   C. Synthesis—multi-step
   D. Activity—good
   E. Cost—high
4. Arnold, ICI, U.S. Pat. No. 5,232,918
   A. Links cephalosporin with substituted quinolone nucleus (not quinolone antibiotic)
   B. Linking agent—acid chloride of quiniolone
   C. Synthesis—multi-step
   D. Activity—good
   E. Cost—high
5. Haskell, Warner-Lambert, U.S. Pat. No. 4,404,201
   A. Links cephalosporin-quinolone nucleus (not quinolone antibiotic)
   B. Linking agent—imidazole
   C. Synthesis steps—multiple
   D. Activity—good
   E. Cost—high For example, the fluoroquinolone antibiotic inhibits DNA synthesis in the bacteria; Cell wall synthesis is inhibited by the beta lactam antibiotic; and protein synthesis of the bacterial cell is stopped by a wide variety of antibiotics, e.g., tetracyclines, metronidazole, chloramphenicol, clindinomycin, aminoglycosides, erythromycin, azithromycin and vancomycin. The last named, vancomycin, is also a cell wall synthesis inhibitor and has been the antibiotic of choice in attacking staphylococcus infections.

DEFINITIONS OF BETA-LACTAMS

There are a number of classes of antibiotics which may be designated "beta-lactams."

1. Penicillins
2. Cephalosporins
3. Monobactams
4. Carbapenems

All four classes of beta-lactams process several features in common:

1. a 4-membered ring termed a β-lactam ring. This ring is chemically sensitive to acid and to some bacterial enzymes.
2. Three of the four types have a ring fused to the β-lactam ring, but not the monobactam type.
3. All possess a carboxyl group pendant to the ring fused to the β-lactam ring, or a carboxyl group on a side chain pendant to the β-lactam ring.
4. All possess an amino or hydroxyl group on the pendant side chain of the β-lactam ring.

From a microbial point of view all four classes of β-lactams interfere with cell wall synthesis of bacteria.

These four classes of antibiotics have been designated as "beta-lactams" in modern pharmacology books. See, for example, pages 724–737 of Chapter 43 in *"Basic and Clinical Pharmacology,"* B. G. Katzung, Appleton and Lange, $7^{th}$ edition, 1998, Stamford, Conn.

SUMMARY OF THE INVENTION

The general formula for the three antibiotic species is given below

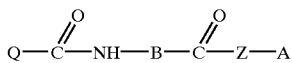

in which Q is a Quinolone antibiotic joined to a Beta-lactam antibiotic B by means of an amide group, or an ester group, and the Beta-lactam antibiotic is then joined by means of a linkage.

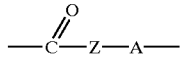

in which Z is an oxygen or a nitrogen atom, and A is an antibiotic drawn from the following group:

1. Tetracyclines (all)
2. Metroindazole
3. Chloramphenicol
4. Clindinamycin
5. Aminoglycosides (all)
6. Erythromycin
7. Azithromycin
8. Vancomycin The initial step in these syntheses is the conversion of the Quinolone to an acid chloride by means of reaction with thionyl chloride. The second step is the reaction of the Quinolone acid chloride with a Beta-lactam type bearing an amino group. The third step is the conversion of the carboxyl group of the Beta-lactam molecule to an acid chloride utilizing the reagent triphenyl phosphine and carbon tetrachloride. The fourth step in the reaction sequence is the reaction of the Beta-lactam acid chloride with the third component drawn from the list of eight antibiotics above, which forms with an amide linkage or an ester linkage.

The three-component antibiotic produced is suitable for the treatment of a wide variety of bacterial infections in man and animals, and will reduce substantially the possibility that antibiotic resistant strains of bacteria will develop.

It will be noted that the chemistry has been selected to avoid structural changes in the components, and chirality is also maintained.

DETAILED DESCRIPTION OF THE INVENTION

I. Composition of Three Antibiotics

The synthesis of the general formula

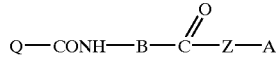

for the antibiotic composition is detailed below, in which Q—is a quinolone, B—is a Beta-lactam, Z—is an oxygen or nitrogen and A is a third component, an antibiotic.

The initial step is the conversion of a Quinolone to the corresponding acid chloride

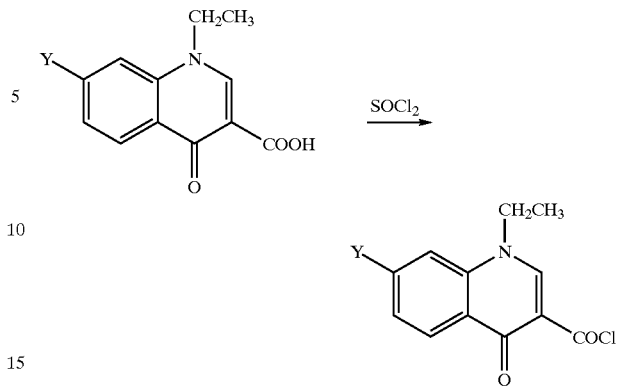

in which R is an alkyl group and Y is an amine substituted group without a free amine group Ofloxacin

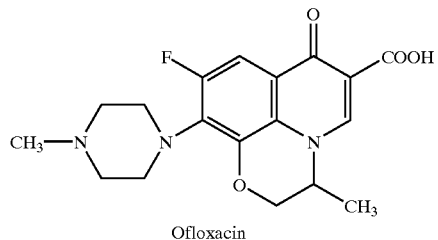

Ofloxacin and Nalidixic Acid

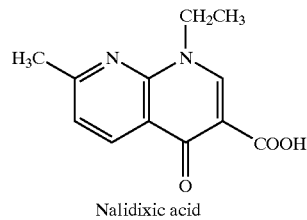

Nalidixic acid and Pefloxacin

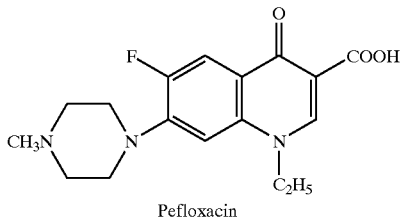

Pefloxacin are example Quinolone antibiotics.

The conversion to the corresponding acid chlorides is straightforward and utilizes $SOCl_2$.

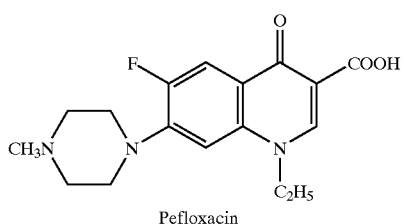
Pefloxacin

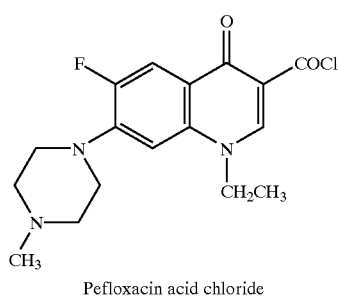
Pefloxacin acid chloride

There are no isomers resulting from this reaction, the product is a singular one immediately useful in the synthesis sequence.

The reaction with nalidixic acid, or Ofloxacin is analgous to the Pefloxacin reaction, when thionyl chloride is the reagent for conversion to the acid chloride.

The presence of the quinolone component inhibits the DNA gyrase enzyme essential to bacterial multiplication.

The second step in the synthesis sequence is the condensation of the Quinolone acid chloride with the Beta-lactam type antibiotic. The purpose of this component is to cause inhibition of the cell wall synthesis by bacteria.

The following penicillins will be employed:

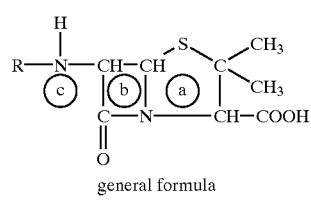
general formula in which R is:

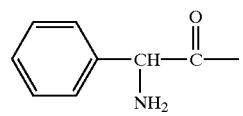
ampicillin

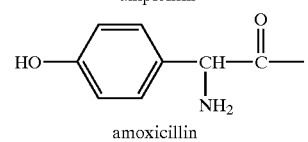
amoxicillin

The following Cephalosporins will be employed:

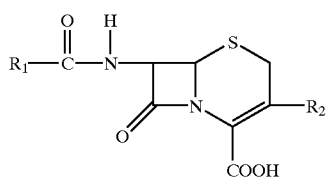

wherein $R_1$ and $R_2$ are as listed,

| $R_1$ | $R_2$ | Name |
|---|---|---|
| phenyl-CH(NH$_2$)- | —CH$_3$ | Cephalexin |
| cyclohexadienyl-CH(NH$_2$)- | —CH$_3$ | Cephradine |
| 4-HO-phenyl-CH(NH$_2$)- | —CH$_3$ | Cefadroxil |
| phenyl-CH$_2$(NH$_2$)- | —Cl | Cefaclor |
| 2-amino-thiazolyl-C(=N-OCH$_3$)- | —CH$_2$OCOCH$_3$ | Cefloxamine |

-continued

| $R_1$ | $R_2$ | Name |
|---|---|---|
| 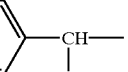 | 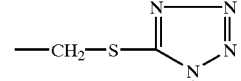 | Cefamandole |
| 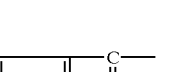 | 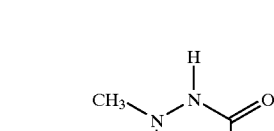 | Ceftriaxone |
| 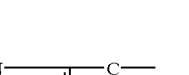 | —H | Ceftizoxime |

The following miscellaneous types:

Carbapenems

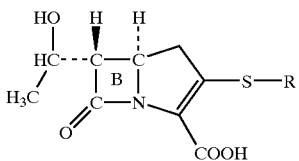

R: 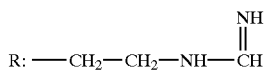

Monobactam

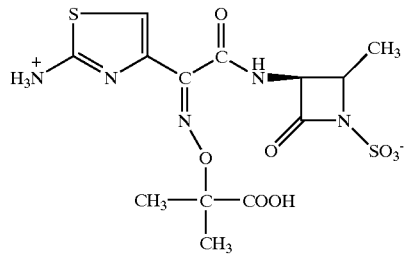

The coupling of component 1, the Quinolone acid chloride with the componene 2, the Beta-lactam and related components gives the general formula

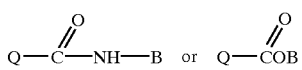

in which Q is the acid chloride which interacts with an amino group on the Beta-lactam or related structure, to give an amide, or reacts with an hydroxyl group on the Beta-lactam or related structure to give an ester. The reaction is conducted in pyridine, the presence of which maintains a medium in which the Beta lactam structure is stable.

An example typical of the amide type formation is given below:

General Formula

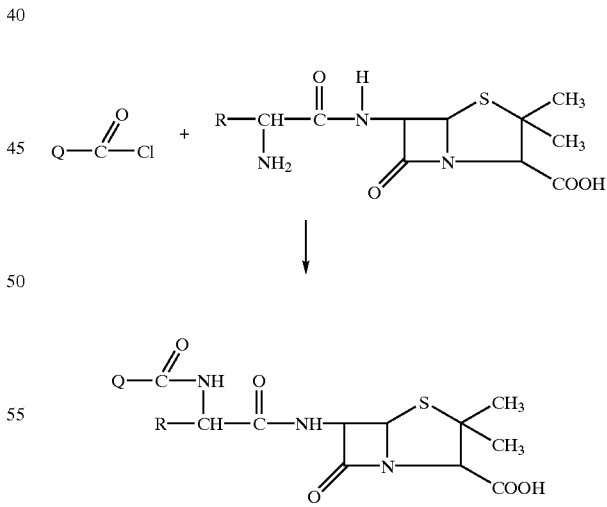

Specific example:

The condensation of a quinolone acid chloride, nalidixic acid chloride with ampicillin

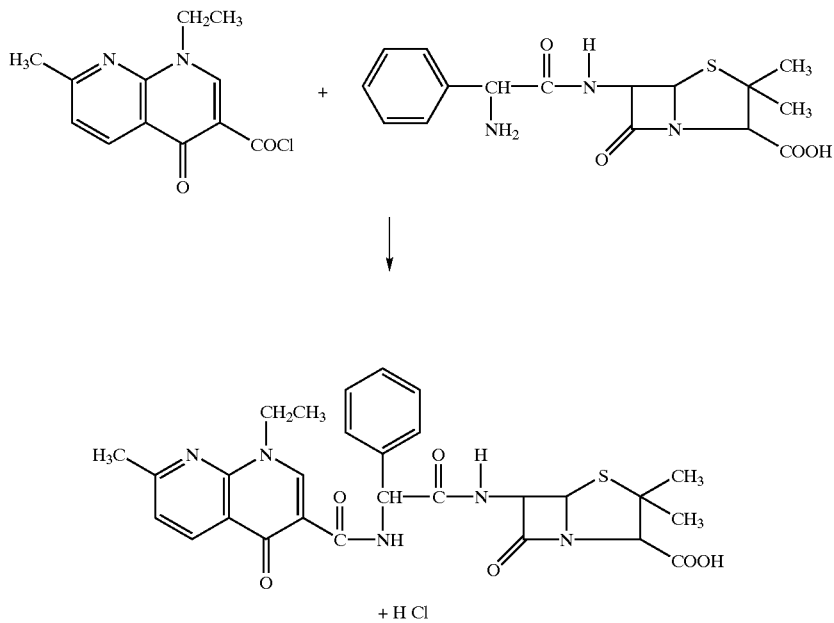

At the conclusion of the reaction the HCl is neutralized by the addition of the stoichometric quantity of sodium bicarbonate. (See Experimental for details).

The reactions with all Quinolone acid chlorides with the Beta Lactams and related carbapenems, and monobactams are conducted in analogous fashion.

A specific example of the condensation of a Quinolone acid chloride with an amino group bearing Beta-lactam or related carbapenems or monobactam is given below:

The coupling of the third component to the first two is further accomplished as described below.

The general formula for the product is

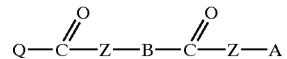

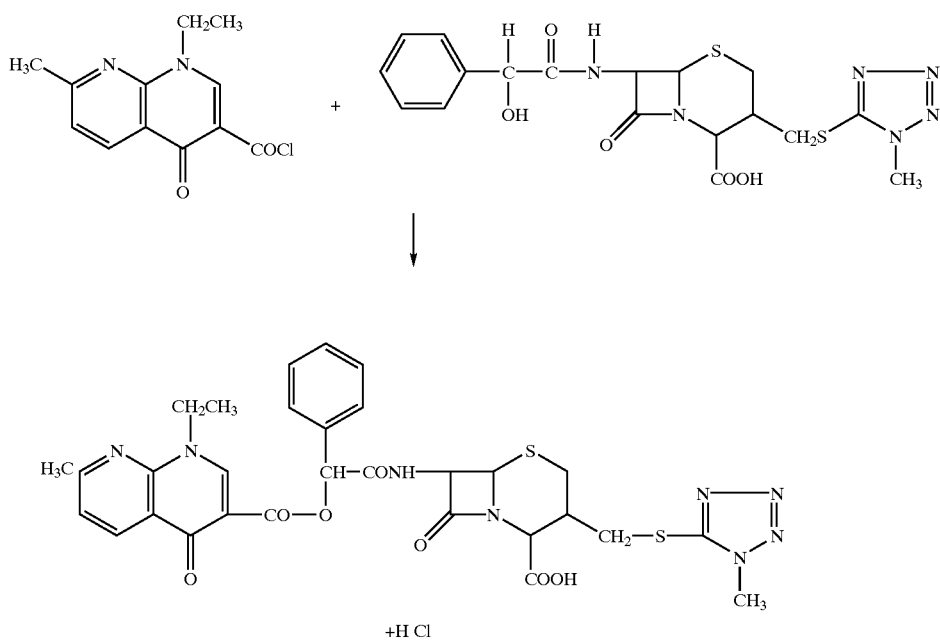

in which Q is a Quinolone, Z is Oxygen (as in an ester) or N (as in an amide), B is a Beta-lactam or monobactam, or carbapenem, and A is an antibiotic drawn from the list noted above in the "Summary of the Invention" and also below.

"A" List

1. Tetracyclines—(all)
2. Metronidazole

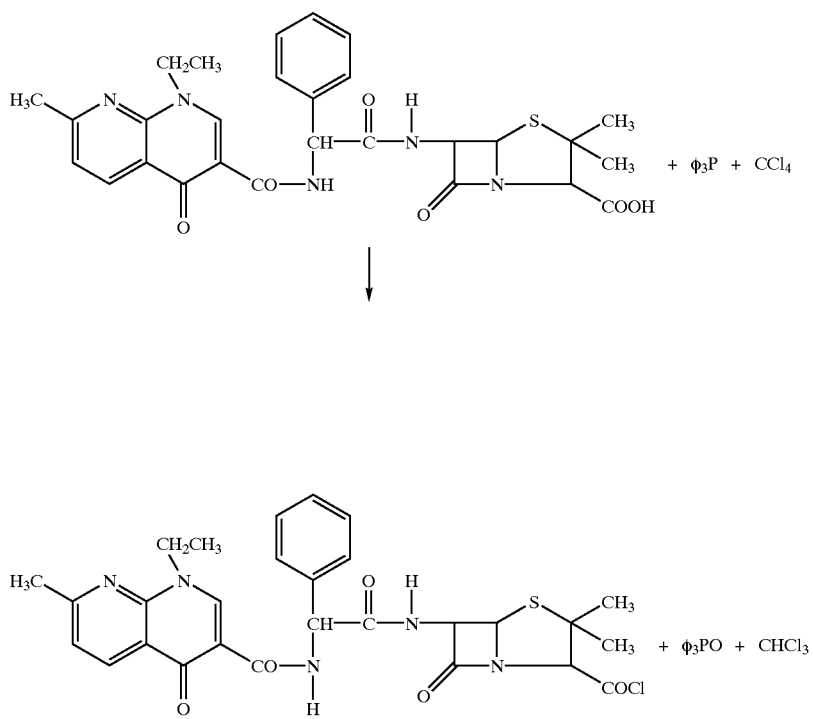

3. Chloramphenicol
4. Clindinamycin
5. Aminoglycosides—(all)
6. Erythromycin
7. Azithromycin
8. Vancomycin The initial step in the addition of the third component is the conversion of the first two components, synthesized above, to an acid chloride utilizing an unusual reaction of carboxyl groups with triphenylphosphine and carbon tetrachloride which does not generate acid which would destabilize the Beta-lactam type structures.

An example of the reaction is,

All quinolones (listed above Ofloxacin, and nalidixic acid and pefloxacin) and the β-Lactam and related structures and their condensation products react in analogous fashion with triphenyl phosphine and carbon tetrachloride in order to form the acid chloride.

The coupling of the third component to the acid chloride formed of the two components, just described above, is carried out in pyridine solution with the antibiotics in the "A" as below:

1. Tetracycline

Doxycycline will be utilized to demonstrate coupling to the "two component" acid chloride, but all generic tetracyclines may be utilized.

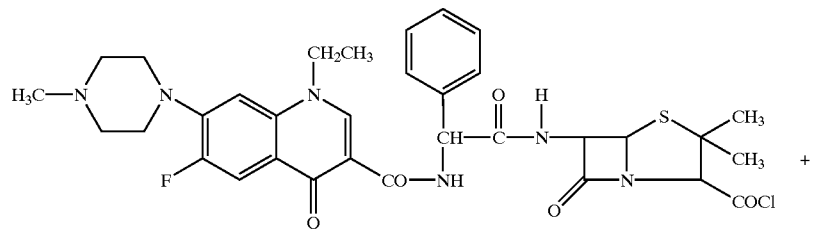

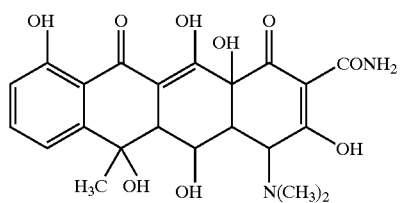

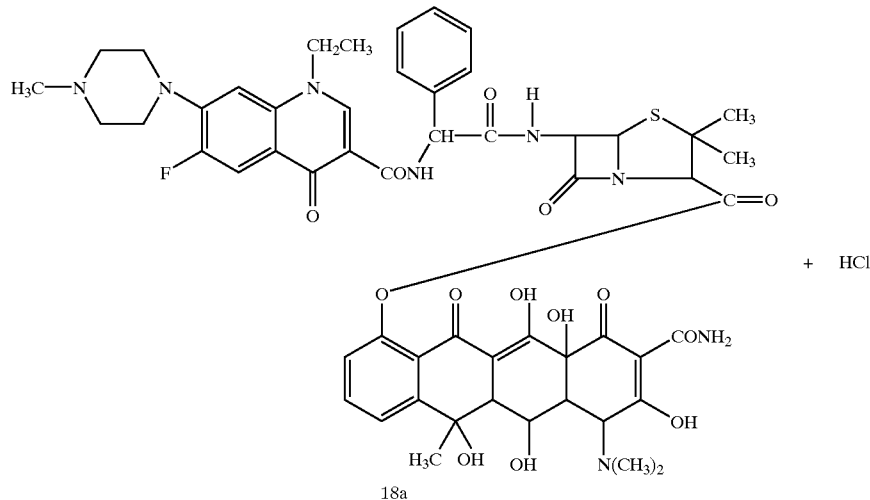

The phenolic group is the most neucleophilic group in the tetracycline molecule and will be preferentially attacked by the acid chloride.

Chlortetracycline, oxytetracycline, tetracycline, demeclocycline, methacycline and minocycline will react with the "2-composition" acid chloride in the analagous fashion.

2. Metronidazole

The acid chloride resulting from the condensation of pefloxacin and ampicillin followed by reaction with triphenylphosphine and carbon tetrachloride reacts with metronidazole as follows:

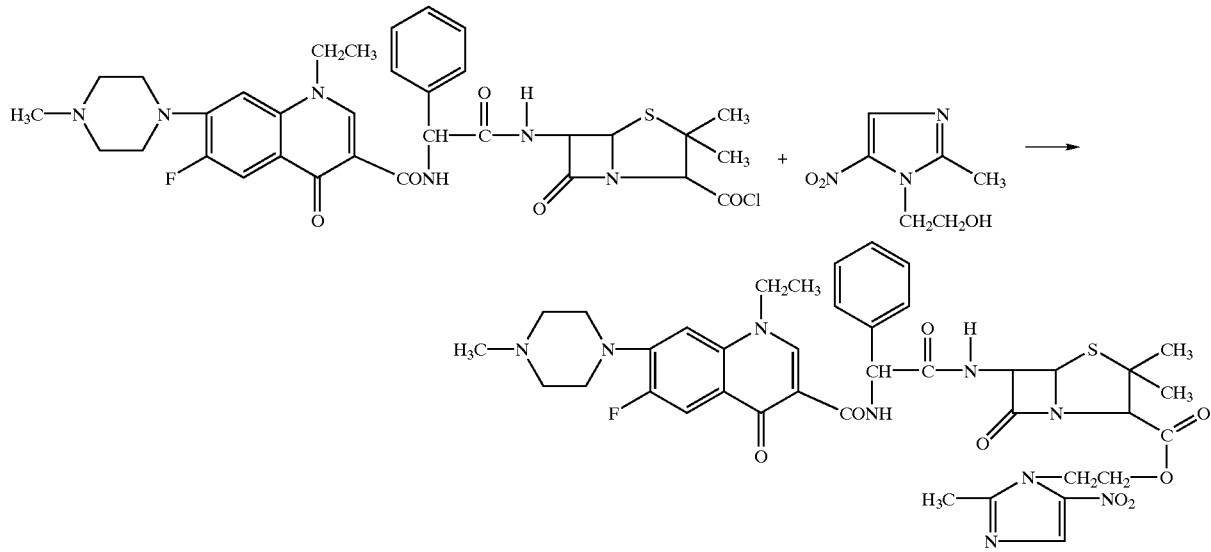

The hydroxy ethyl group of the imidazole is attacked by the acid chloride to form the ester.

3. Chloramphenicol

The acid chloride, resulting from the condensation of pefloxacin and ampicillin, followed by the reaction with triphenylphosphine and carbon tetrachloride, reacts with chloramphenicol as follows:

4. Clindinamycin

Clindinamycin is one of the few antibiotics which are effective against anaerobic infections and is used particularly with gentamycin for belly wounds and septic abortions.

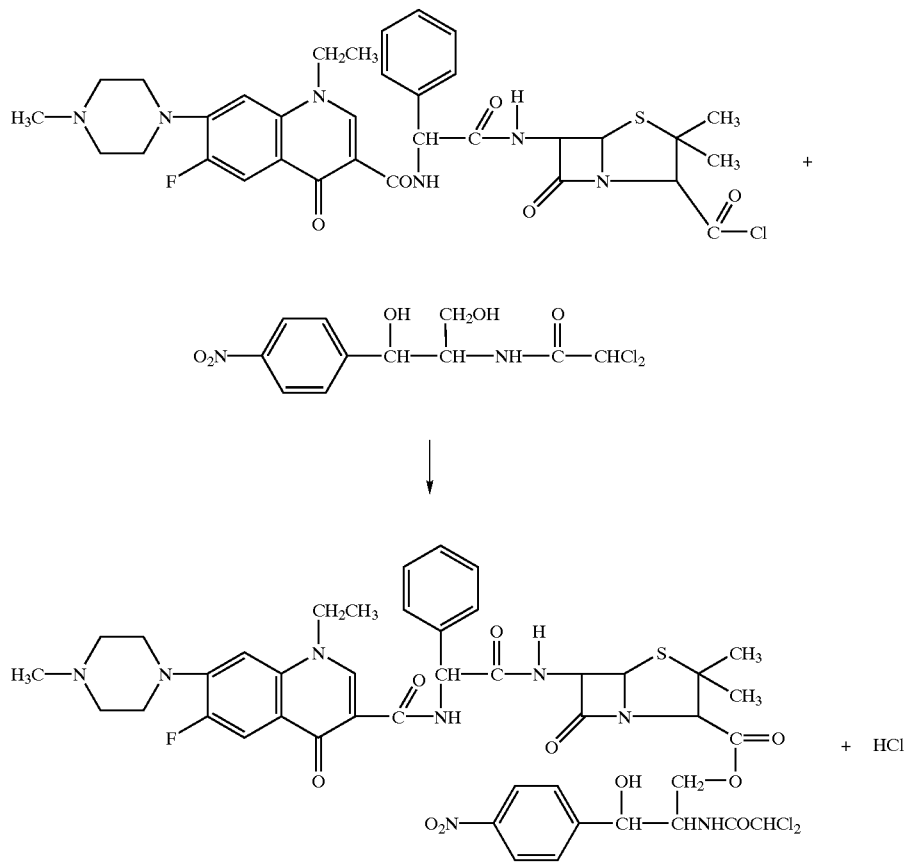

The acid chloride resulting from the condensation of pefloxacin and ampicillin, followed by the reaction with triphenylphosphine and carbon tetrachloride reacts with clindinamycin as follows, the secondary hydroxyl adjacent to the S—CH$_3$ group on the ring being the most neucleophilic.

5. Aminoglycosides

The aminoglycoside example utilized will be gentamycin C$_1$, but gentamycin C$_2$, gentamycin C$_1$, kanamycin, amikacin and tobramycin will react analogously in the coupling scheme outlined below. For the example, gentamycin C$_2$ will be utilized.

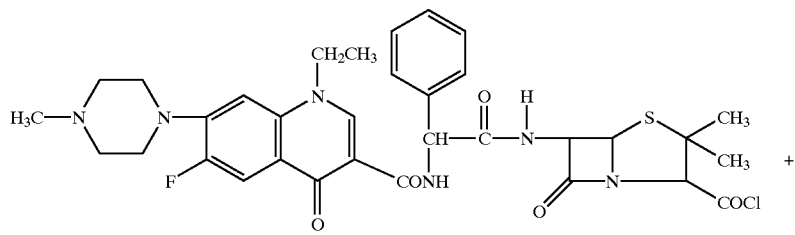

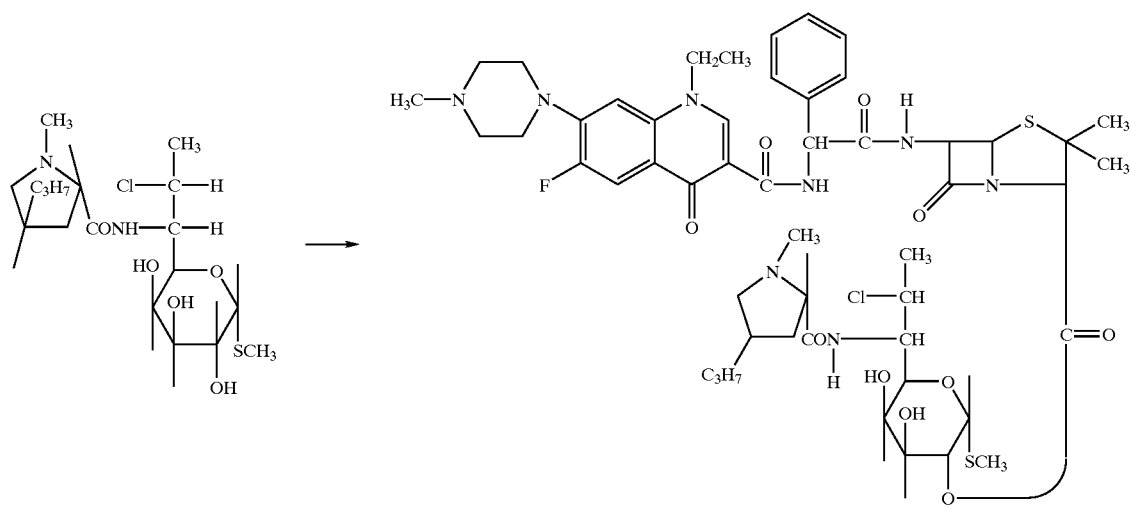

The acid chloride resulting from the condensation of pefloxacin and ampicillin followed by reaction with triphenylphosphine and carbon tetrachloride reacts with gentamycin C$_1$, as follows:

Formula I

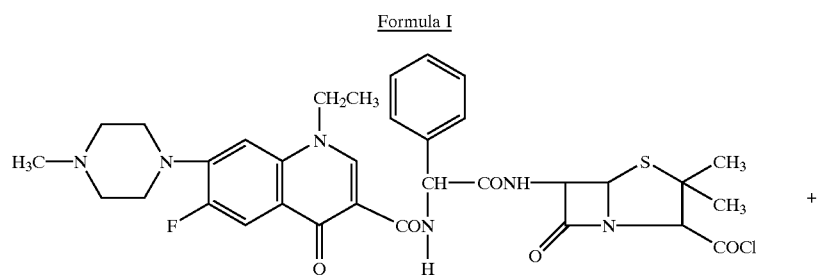

-continued

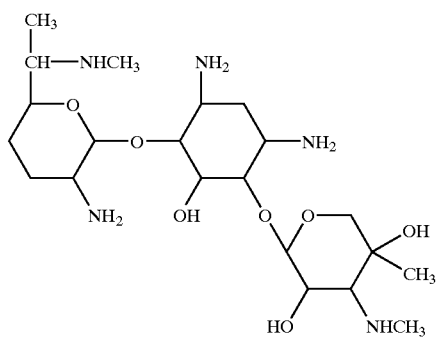

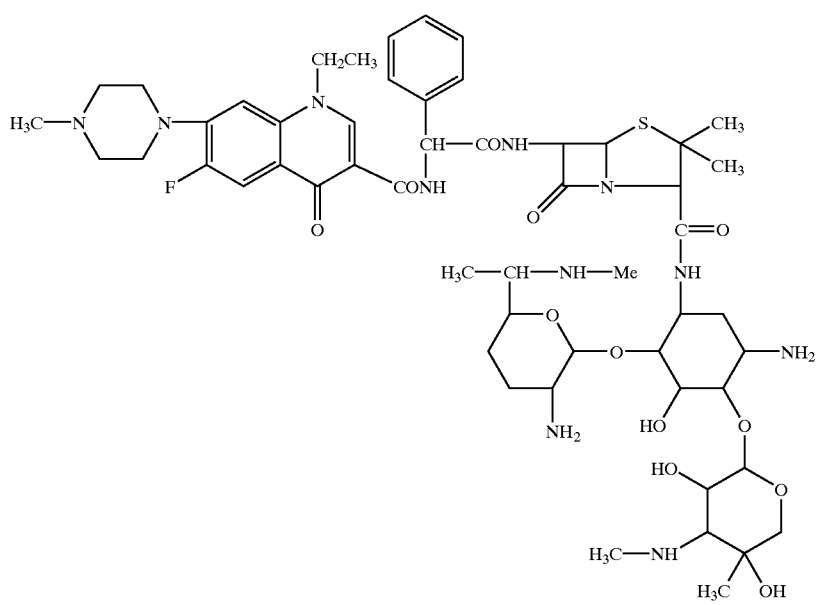

All of the primary amino groups are essentially equivalent chemically, thus all three can be seen as yielding clinically essentially the same product. It is also true that gentamycins, tobramycin, and netilimicin gave clinically similar results as well as amikacin and kanamycin.

6. Erythromycin—A Macrolide

The acid chloride resulting from the condensation of pefloxacin acid chloride and ampicillin, followed by the reaction with triphenylphosphine and carbon tetrachloride, reacts with erythromycin as follows:

Formula I + Erythromycin ⟶
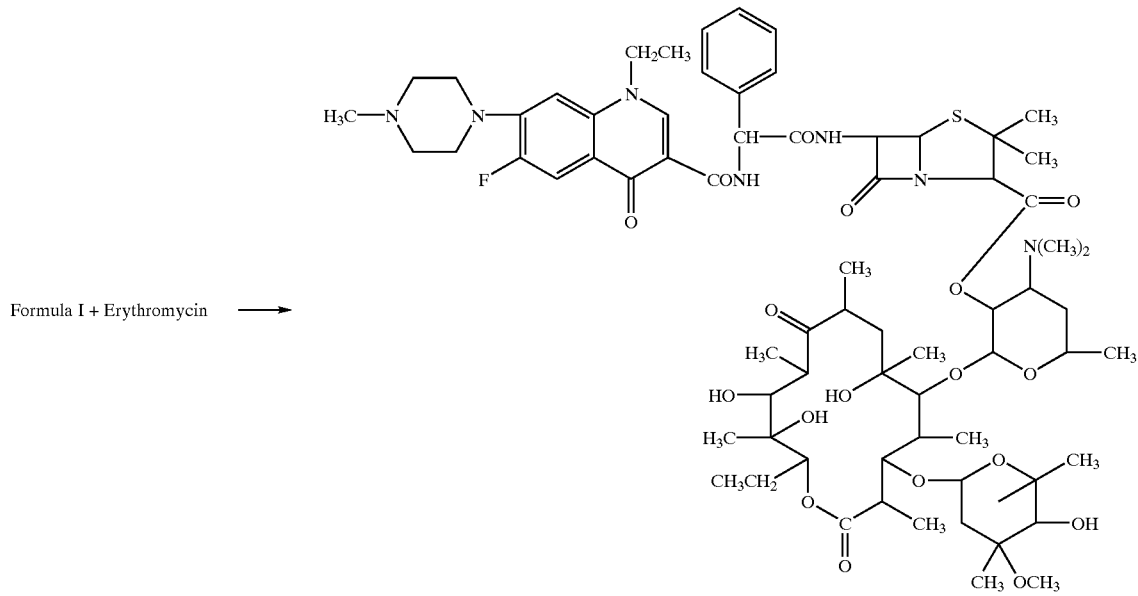
7. Azithromycin—a macrolide
The condensation of the acid chloride Formula I with Azithromycin takes place as follows to give the trio of antibiotics, into a single composition:
Formula I + Azithromycin ⟶
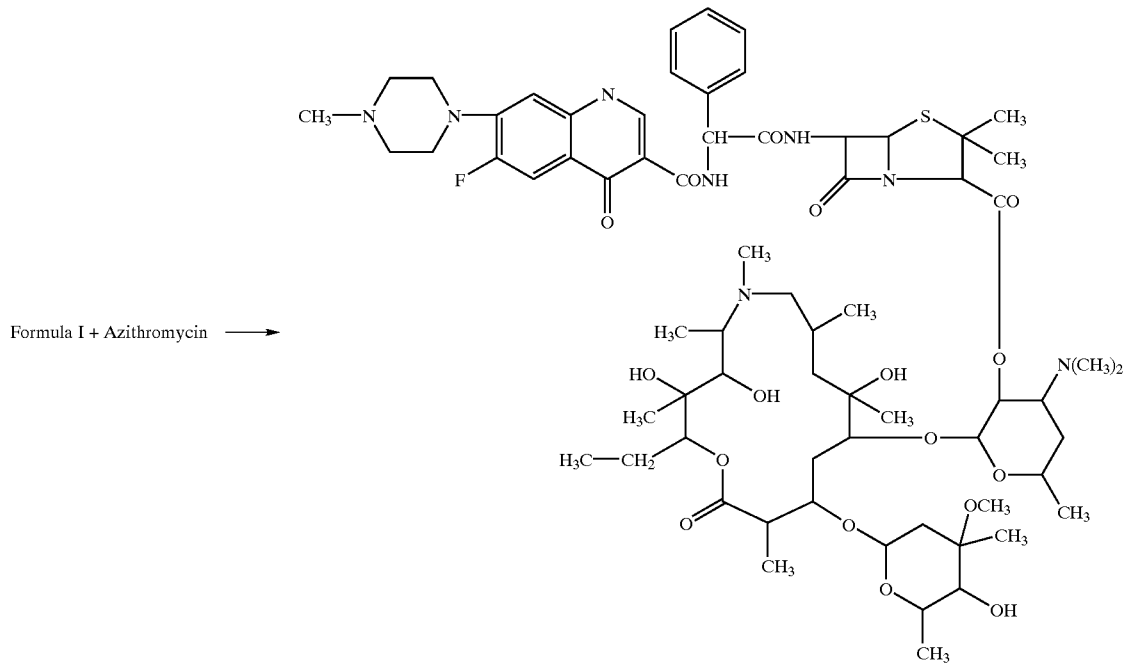

8. Vancomycin

The condensation of the acid chloride Formula I with Vancomycin takes place as below to give the antibiotics into a single composition. The free amino group is the most neucleophilic group and reacts with the acid chloride (Formula I) preferentially.

Formula I + Vancomycin ⟶

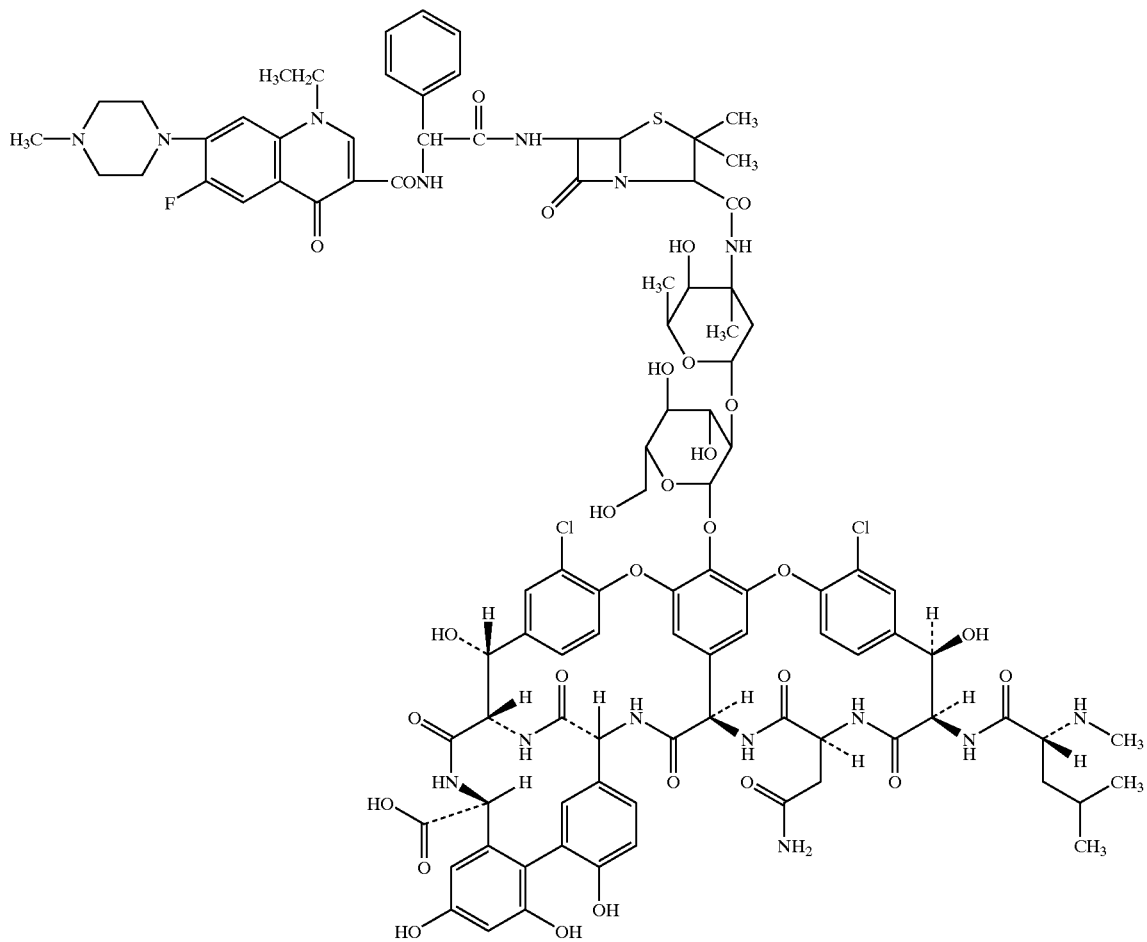

Procedure B—The Condensation of a Quinolone Acid Chloride with a Beta Lactam, Carbapenem, or Monobactam (all of which possess a pendant amino or hydroxyl group.

The reactions are all conducted at the 0.01 mole scale, employing the product of reaction of "A" above. The residue from reaction "A" above is taken up in 25 ml of dry pyridine in a 50 ml RB flask equipped with stirrer, thermometer and a means of heating and or cooling.

Experimental

Procedure A—Conversion of Quinolones to Acid Chlorides

The conversion of all quinolone compounds possessing a free carboxyl group, but not a free amino group, is carried out by using an excess of thionyl chloride as the reactive agent by the procedure according to Shriner, et al, *The Systematic Identification of Organic Compounds*, John Wiley, 1948. To 0.01 mole of the quinolone acid is added 5 ml of thionyl chloride and the reaction is carried out in a 50 ml RB flask equipped with a reflux condenser, stirrer and thermometer and heating mantle and the reaction maintained at 50° C. for 4 hours, or until the evolution of $SO_2$ and HCl ceases.

The reaction product is obtained by evaporating the liquid solution to dryness at reduced pressure at 0° C. At all times the product must be protected from moisture. The residue product is retained for the next reaction in the sequence, the reaction of the quinolone acid chloride with the Beta-lactam type antibiotic, i.e. the penicillin, cephalosporin, carbapenem or monobactam.

EXAMPLE:

The amoxicillin Beta-lactam, 0.01 mole is added to the pyridine solution of the acid chloride portionwise, not allowing the temperature to exceed 50° C. The reaction is maintained at 50° C. for an additional 4 hours and reaction is neutralized with 0.01 mole of $NaHCO_3$ to yield an essentially neutral solution which is then evaporated at reduced pressure and 0° C. to yield a residue of product utilized in the following reaction, "C," of the acid chloride from reaction "B".

Procedure C—The Conversion of the Product B to an Acid Chloride via Treatment with Triphenyl Phosphine and Carbon Tetrachloride In order to avoid the destruction of the Beta-lactam structure by acid, the caroxyl group present in Formula I type products, from the condensation of the quinolone acid chloride with the Beta-lactam type structures, the acid chloride is formed using the reaction of the carboxyl group with triphenyl phosphine and carbon tetrachloride to yield the acid chloride, triphenyl phosphine oxide and chloroform.

The procedure is that of *J. Org. Chem.*, 48, 3727 (1983) for the preparation of Beta-naphthoyl chloride from Beta-napthoic acid, triphenyl phosphine resin and carbon tetrachloride.

The residue product from "B" above Formula I is dissolved in 25 ml of dry carbon tetrachloride, placed in a 50 ml RB flask equipped with stirrer, thermometer, reflux condenser. To the stirred solution at ambient temperature 0.01 mole of triphenyl phosphine is added and the reaction maintained at reflux for 4 hours. At the completion of the reaction the phosphine product is evaporated to dryness under vacuum at 0° C. to yield the acid chloride product.

Procedure D—Condensation of the Acid Chloride from "C" Above with an Antibiotic Possessing a Reactive Hydroxyl Group, Said Antibiotic Possessing the Capability of Inhibiting Bacterial Protein Synthesis The residue from Reaction "C" above is reacted with 0.01 mole of any antibiotic selected from list "A" in the Detailed Discussion of the Invention above.

The reaction product from "C" above, Formula was placed in 25 ml of pyridine solution in a 50 ml RB flask equipped with reflux condenser, stirrer, thermometer and heating mantle. To the stirred mixture 0.01 mole of the antibiotic form list "A" was added and the reaction heated to 50° C. and maintained at the temperature for 4–8 hours. At the conclusion of the reaction 0.01 mole of $NaHCO_3$ was added in small portions to neutralize the HCl product. The product was isolated by evaporation to dryness.

Procedure E—Condensation of Antibiotic Containing a Free Amine or Secondary Amine Group The method is analagous to the just described steps "A," "B" and "C" for antibiotics containing a primary hydroxyl group, or phenolic hydroxyl.

Product characterization—all products are characterized utilizing FTIR spectra to determine the presence of the acid chloride, and ester or amide bands as appropriate.

Final products contain a minimum of by products and can be evaluated, without purification, or by liquid chromatography or TLC, for antimicrobial activity.

All compounds will obviously be active and the most active easily selected by classical antibiotic sensitivity tests.

To summarize, the preferred process steps for forming the two-antibiotic composition, followed by the steps to form the three-antibiotic compositions follows:

1. A fluoroquinolone is converted to the fluoroquinolone acid chloride via reaction with thionyl chloride.

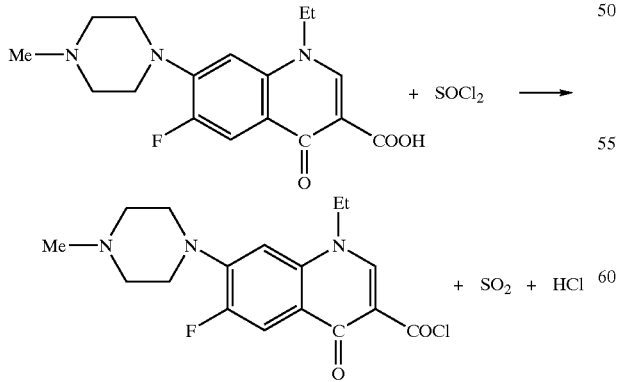

This is a clean single step reaction with no isomers or byproducts formed, that is carried out under mild conditions.

2. The second step involves the reaction of the fluoroquinolone acid chloride with a beta-lactam possessing a pendant OH (hydroxyl) or $NH_2$ (amino) to form an ester or an amide. Since the β-lactams are all sensitive to acid which will lead to a destruction of the β-lactam ring, the reaction is carried out in a basic solvent, pyridine. The pyridine solvent will prevent the HCl formed from attacking the β-lactam ring.

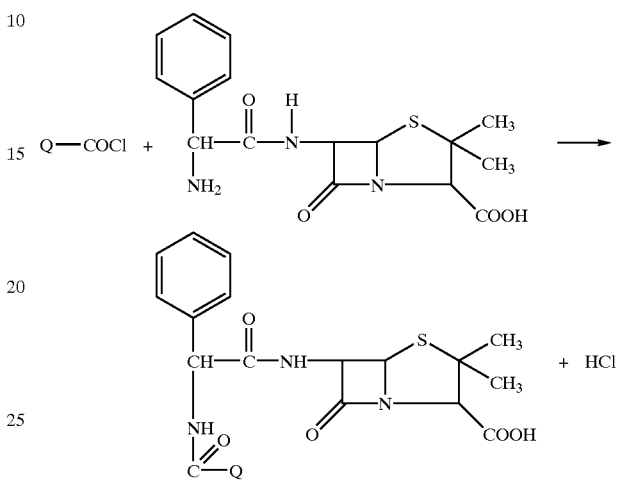

3. The third step involves the conversion of the single composition of two antibiotics produced in step 2 to the corresponding acid chloride. This conversion of the pendant carboxyl group to the corresponding acid chloride is achieved without the formation of the acidic byproduct by the following general reaction:

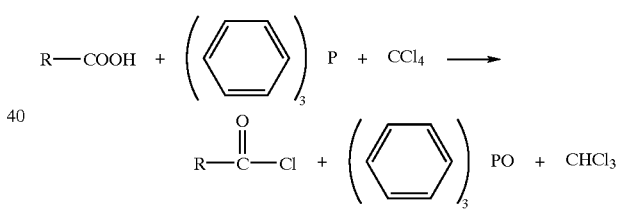

The acid reacts with triphenyl phosphine and carbon tetrachloride to form the acid chloride, triphenyl phosphine oxide and chloroform under mild conditions.

4. The fourth step involves the condensation of the acid chloride product of step 3 with one of the antibiotics from the following group: tetracycline, metronidazole, chloramphenicol, clindinamycin, an aminoglycoside, erythromycin, azithromycin, vancomycin, all of which posses a pendant OH, NH, or $NH_2$ and react with the acid chloride to form an ester (with the pendant OH) or an amide (with the pendant NH or $NH_2$). Specifically,

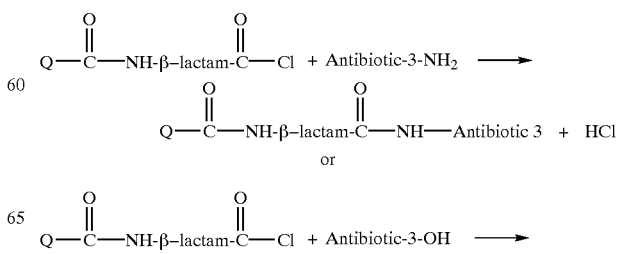

-continued

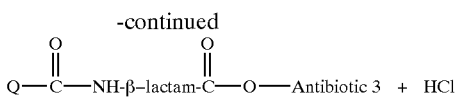

What is claimed is:

1. Process for preparing a compound from a plurality of antibiotics comprising, in sequence:
   a. treating a quinolone selected from the group consisting of nalidixic acid, perfloxacin, and ofloxacin with thionyl chloride to produce the corresponding quinolone acid chloride;
   b. condensing said quinolone acid chloride in a solvent consisting of pyridine, with a β-lactam selected from the group consisting of cephalosporins selected from the group consisting of cephalexin, cephradine, cefadroxil, cefaclor, cefloxamin, ceftriaxone and ceftizoxime and penicillins selected from the group consisting of ampicillin and amoxicillin to form a compound having two antibiotic functions and HCl;
   c. adding a stoichiometric quantity of bicarbonate of sodium to neutralize the HCl formed in step (b) and forming $CO_2$ and an inert alkali or alkaline earth metal chloride and said compound having two antibiotic functions:
   d. removing the solvent used in step (b) and the $CO_2$ formed in step (c) by evaporation in vacuo to isolate said compound having two antibiotic functions and said inert chloride.

2. Process for preparing a compound from a plurality of antibiotics comprising, in sequence:
   a. treating a quinolone selected from the group consisting of nalidixic acid, perfloxacin, and ofloxacin with thionyl chloride to produce the corresponding quinolone acid chloride;
   b. condensing said quinolone acid chloride in a solvent consisting of pyridine, with a β-lactam selected from the group consisting of cephalosporins selected from the group consisting of cephalexin, cephradine, cefadroxil, cefaclor, cefloxamin, ceftriaxone and ceftizoxime and penicillins selected from the group consisting of ampicillin and amoxicillin to form a compound having two antibiotic functions and HCl;
   c. adding a stoichiometric quantity of bicarbonate of sodium to neutralize the HCl formed in step (b) and forming $CO_2$ and an inert alkali or alkaline earth metal chloride and said compound having two antibiotic functions;
   d. removing the solvent used in step (b) and the $CO_2$ formed in step (c) by evaporation in vacuo to isolate said compound having two antibiotic functions and said inert chloride;
   e. mixing said compound having two antibiotic functions with a triaryl phosphine and carbon tetrachloride, to form an acid chloride of said compound having two antibiotic functions;
   f. mixing said acid chloride formed in step (e) with said solvent used in step (b) with a third compound selected from the group consisting of tetracycline, metronidazole, chloramphenicol, clindamycin, erythromycin, azithromycin and vancomycin to produce a compound having three antibiotic functions and HCl, chloroform and solid inert triarylphosphine oxide;
   g. removing HCl, chloroform and said solvent to isolate said compound having three antibiotic functions and said inert triphenylphosphine oxide, by evaporation in vacuo;
   h. dissolving the isolated materials formed in step (g) and pouring said materials onto a column of alumina or silica gel;
   i. adding successive polar solvents with a small amount of ethanol to separate said triarylphosphine oxide from said compound having three antibiotic functions.

* * * * *